(12) United States Patent
Musso et al.

(10) Patent No.: US 6,755,196 B2
(45) Date of Patent: Jun. 29, 2004

(54) IRRIGATION DRAPE

(76) Inventors: Emilio Musso, 550 Sandpiper Way, Boca Raton, FL (US) 33431; John Levin, 219 Churchill Rd., West Palm Beach, FL (US) 33405

( * ) Notice: Subject to any disclaimer, the term of this patent is extended or adjusted under 35 U.S.C. 154(b) by 34 days.

(21) Appl. No.: 10/260,199

(22) Filed: Sep. 27, 2002

(65) Prior Publication Data

US 2004/0060566 A1 Apr. 1, 2004

(51) Int. Cl.[7] ................................................ A61F 5/37
(52) U.S. Cl. ...................... 128/849; 128/850; 128/851; 128/852; 128/853; 128/854; 128/855; 128/856
(58) Field of Search ............................... 128/849, 850, 128/851, 852, 853, 854, 855, 856

(56) References Cited

U.S. PATENT DOCUMENTS

| 3,853,329 | A | * | 12/1974 | McDonald | 280/47.35 |
|---|---|---|---|---|---|
| 4,598,458 | A | * | 7/1986 | McAllester | 128/853 |
| 4,769,003 | A | | 9/1988 | Stamler | |
| 4,998,538 | A | * | 3/1991 | Charowsky et al. | 128/856 |
| 5,005,590 | A | * | 4/1991 | Eldridge et al. | 128/849 |
| 5,161,544 | A | * | 11/1992 | Morris | 128/849 |
| 5,224,940 | A | * | 7/1993 | Dann et al. | 604/290 |
| 5,312,385 | A | | 5/1994 | Greco | |
| 5,316,541 | A | * | 5/1994 | Fischer | 600/21 |
| 5,349,965 | A | * | 9/1994 | McCarver | 128/846 |
| 5,398,700 | A | * | 3/1995 | Mills et al. | 128/853 |
| 5,415,180 | A | * | 5/1995 | Horan | 128/846 |
| 5,435,322 | A | * | 7/1995 | Marshall | 128/849 |
| 5,609,163 | A | * | 3/1997 | Beard | 128/846 |
| 5,640,975 | A | * | 6/1997 | Diao | 128/853 |
| 5,792,125 | A | * | 8/1998 | Webb | 604/317 |
| 5,848,998 | A | | 12/1998 | Marasco | |
| 5,941,859 | A | | 8/1999 | Lerman | |
| 5,944,014 | A | * | 8/1999 | Webb | 128/845 |
| 6,070,586 | A | * | 6/2000 | Harroll et al. | 128/849 |
| 6,083,209 | A | | 7/2000 | Marasco | |
| 6,405,389 | B1 | * | 6/2002 | Harty | 4/621 |

* cited by examiner

*Primary Examiner*—Henry Bennett
*Assistant Examiner*—Nihir Patel
(74) *Attorney, Agent, or Firm*—McHale & Slavin, P.A.

(57) ABSTRACT

A disposable surgical kit for use with a lavage instrument provides a three dimensional enclosure to capture splash back and aerosols created by the procedure. The kit has a transparent surgical drape to be fitted to a lavage instrument. The drape has an opening for manual access to the wound. A drain receptacle with an absorbent pad is provided to trap the effluvia.

8 Claims, 2 Drawing Sheets

IRRIGATION DRAPE

FIELD OF THE INVENTION

This invention is related to surgical drapes, more particularly, to a drape used during irrigation of a surgical wound or trauma.

1. Background of the Invention

It is common practice to irrigate wounds and other contusions to the body. Usually, the procedure is used to cleanse the opening and allows a visual assessment of the damage. Also, the irrigation may include an application of medicaments, such as disinfectants, antibiotics, and so forth. In some situations it is necessary to use copious amounts of liquids because of blood flow or contaminants in the wound or both. The effluvia must be maintained in a sanitary manner and disposed of in such a way as to prevent contamination of the surgical area.

Surgical drapes are used for a variety of purposes including absorption of effluvia and covering the adjacent areas of the patient's body to prevent spreading of the liquids. Because of the amount of irrigation required in some instances, the drapes are not sufficient to control the spread of the contaminants.

In situations where a pulsed lavage is used to clean and debride a wound, there is significant splatter and atomization of the contaminated liquid. To contain the air born particles, the drape must have a three-dimensional structure.

2. Description of the Prior Art

U.S. Pat. No. 5,848,998 and U.S. Pat. No. 6,083,209 disclose a wound treatment apparatus which has a flexible transparent envelope surrounding the wound site. The envelope has an aperture for lavage and an open bottom to place into a lavage basin. The irrigation takes place inside a closed space. However, the introduction of pulsed lavage into the container causes the loss of visibility through the envelope because of water droplets and fog on the inner surface. Additionally, the plastic enclosure is fixed about the extremity and is not easily removed during the surgical procedure. This is extremely important to allow a surgeon access to the wound for repeated surgical debridement which is often needed.

Stamler, U.S. Pat. No. 4,769,003, teaches a cone shaped splash-back shield for use in lavage. The shield has a nozzle in the apex of the cone to produce a fine spray. The bottom of the cone is open for drainage. There are no other openings in the sidewalls of the shield.

Lerman, U.S. Pat. No. 5,941,859 is similar to the Stamler patent but has an additional suction opening in the shield.

U.S. Pat. No. 5,312,385 to Greco teaches the use of a cylindrical shield with a lavage aperture and a drain on opposite sides of the cylindrical wall.

What is needed is a flexible drape that prevents splash back and allows the doctor's view and access for the introduction of surgical instruments into the protected area. The drape Further, the drape may be combined with a flexible drain receptacle including a super absorbent so that the entire contaminated apparatus may be easily disposed in the normal procedures.

SUMMARY OF THE INVENTION

Disclosed is a surgical drape for enclosing an area about a wound during lavage. The drape is a transparent sheet of flexible plastic film having a center portion, a margin portion and a periphery. An aperture formed in the center portion of the sheet is adapted to fit about a lavage nozzle. An opening in the margin portion is adapted for manual access to a lavage site, the opening is constructed to prevent escape of lavage during manual access. The surgical drape forms a three-dimensional enclosure about a wound.

The drape is treated on the internal surface with a surfactant or coating to prevent fog and adherence of fluid droplets so the surgeon' view of the wound is not obscured.

The drape is constructed to be easily removable from the extremity so the surgeon can perform debridements and/or irrigate the wound and then easily re-debride the wound, as needed. This is an important procedure in treating complex wound infections.

Additionally, the drape of this invention includes ports to permit wound retractors to be inserted for exposing a larger surface of the wound.

In a further embodiment, an absorbent pad is shaped to be placed in a drain receptacle whereby the surgical drape forms an enclosure about a wound with the absorbent pad disposed in the drain receptacle for use in collection and disposal of fluids.

Accordingly, it is an object of the instant invention to provide an easily disposable, flexible, transparent, surgical drape to contain splash back and aerosols by-products of a wound lavage while permitting access to the wound site.

It is a further object of the instant invention to provide a surgical kit or tray which includes a surgical drape to capture splash back from lavage and a drain receptacle with an super-absorbent pad.

It is another object of the invention to provide a surgical drape that does not interfere with visual inspection of the wound during lavage.

It is yet another object of the invention to provide a surgical drape with sufficient flexibility to conform to various body shapes.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
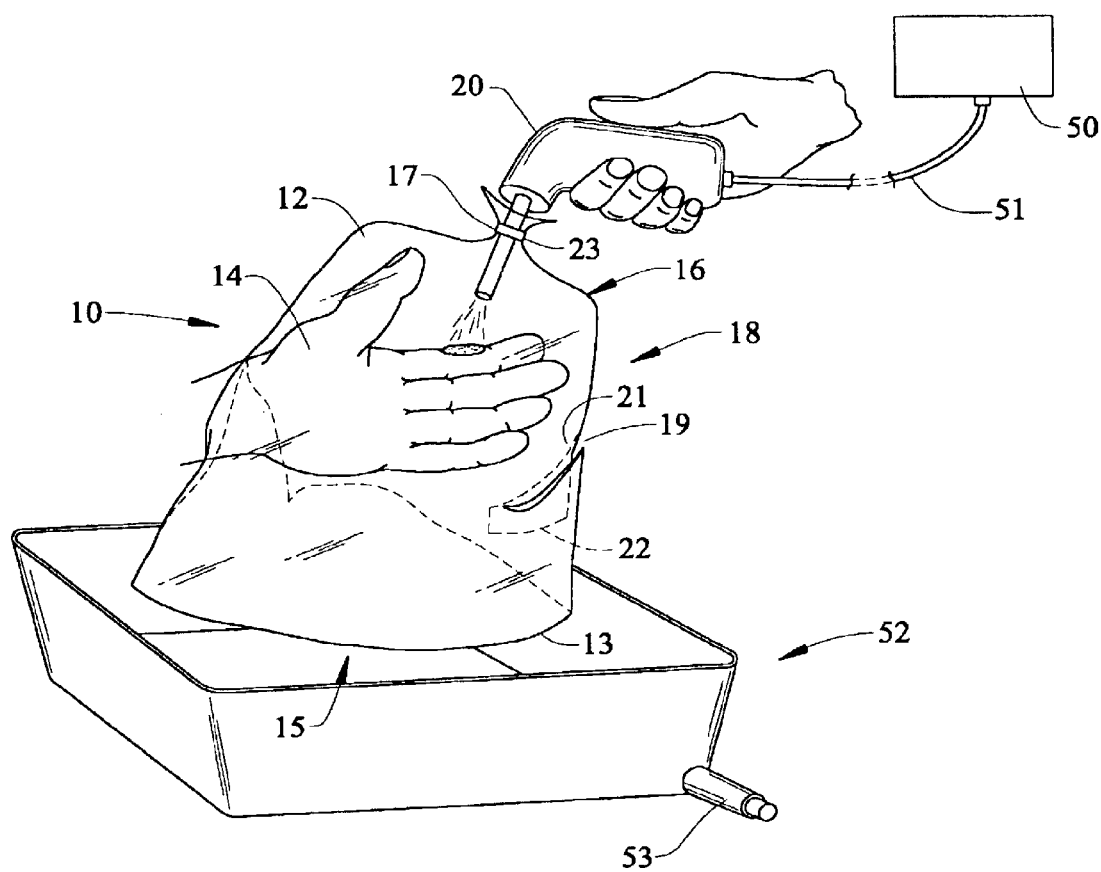
FIG. 1 shows a perspective of the drape in operative position.

The surgical drape 10, shown in FIG. 1, is made of a flexible and transparent sheet 12 of plastic material that is easily sterilized and inexpensive enough to be disposed of after a single use. Also, it is thin enough to easily conform to various body shapes and strong enough to be extended into a three-dimensional tent enclosure about a wound. As shown, the patient's hand 14 is enclosed within a tent shaped enclosure with the periphery 13 defining a mouth 15 of the enclosure. The drape closely conforms to the patient's wrist with no appreciable opening to allow escape of contaminants. The periphery 13 of the drape may be open to a standard surgical basin 52 with a drain 53.

The top portion 16 has an aperture 17 sealed about the irrigation or lavage instrument 20. The lavage instrument is connected to a pump and reservoir 50 by hose 51. The marginal portion 18 extends from the top portion 16 to the periphery 13. Within the marginal portion 18, slits or openings 19 are formed to allow medical personnel to manually access the wound area. The openings 19 are closed by flaps 21 attached to the drape about the openings but having free edges 22. The openings may be closed by other structures, such as tape, Velcro, etc.

The aperture 17 is fastened about its circumference to the irrigation device by adhesive applied to the drape around the aperture or by a tape 23 which can be wrapped around the irrigation nozzle. Of course, other fastening devices may be used to close the aperture about the nozzle.

Once the drape is in place, as shown in FIG. 1, the lavage may proceed. Since the bottom of the tent shaped enclosure is open, air circulation is not impeded. Because the temperature is basically the same inside and outside the tent shaped enclosure, there is little or no condensation on the walls to obscure vision into the enclosure. Also, any droplets on the plastic sheet will freely run off toward the periphery of the drape. The interior of the enclosure may be treated with conventional surfactant compositions to reduce fogging and increase water flow off the drape.

Figure 2:
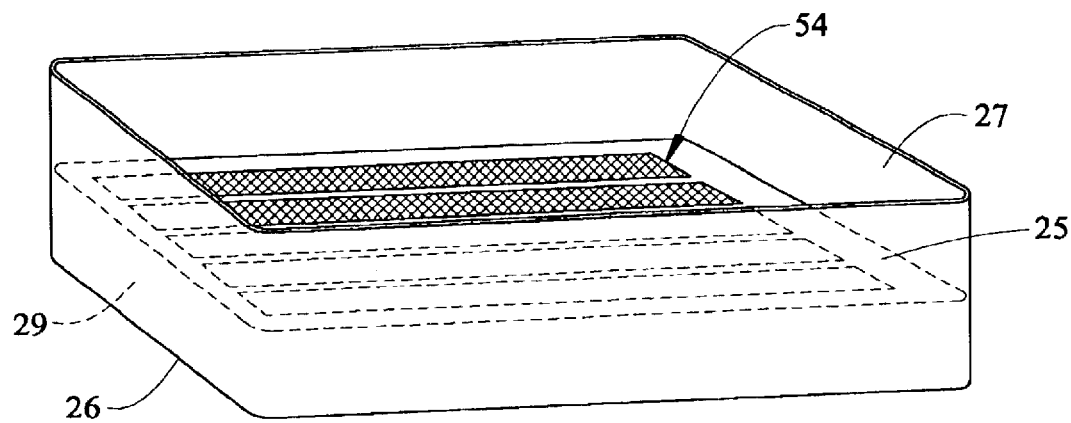
FIG. 2 shows a perspective view of the disposable drain and pad.

FIG. 2 shows the disposable drain with the absorbent pad in place. The pad is overlaid with a screen 54 which may be of plastic or other material of sufficient strength to maintain the pad in place.

Figure 3:
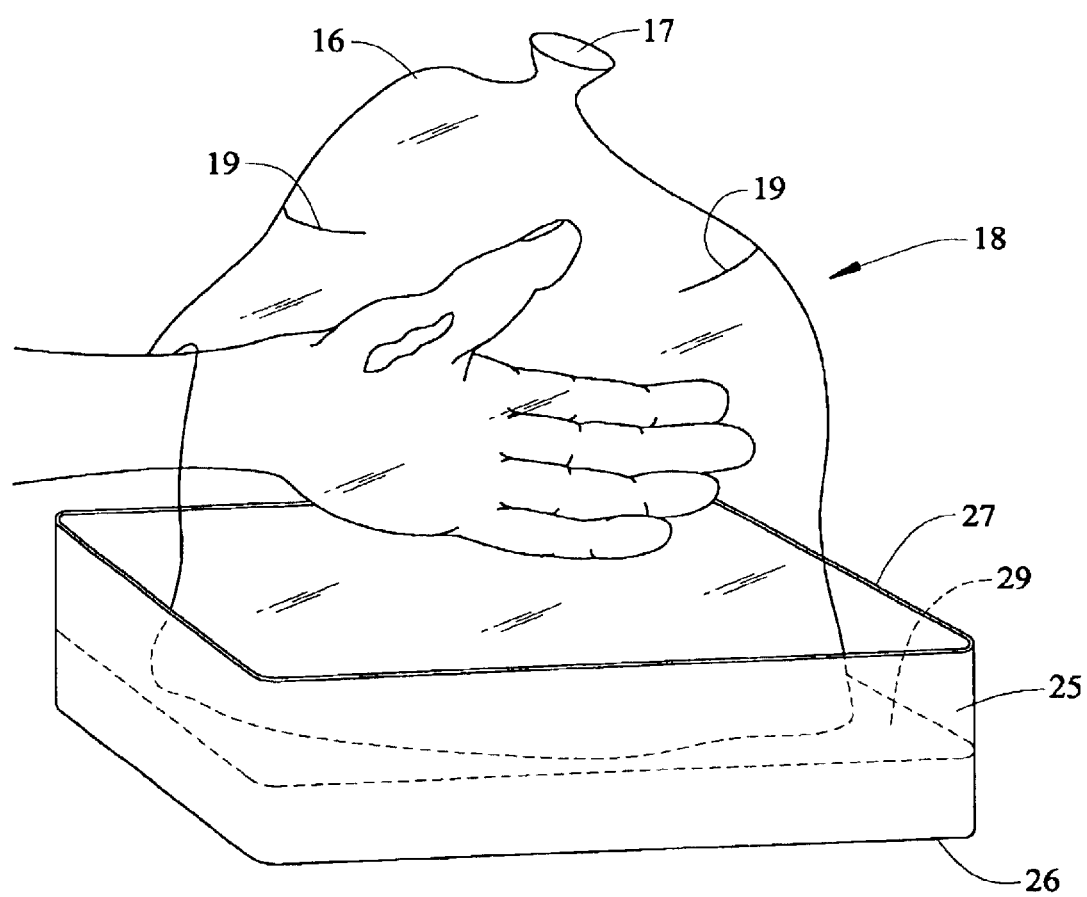
FIG. 3 shows a surgical kit with a surgical drape and the drain.

FIG. 3 illustrates the surgical kit 11 of this invention. The kit would make up a surgical tray used for debridement and lavage and include all necessary disposable elements to be used to treat the afflicted patient. The kit or tray has a surgical drape 10 which can be mounted on a lavage nozzle through aperture 17 and tape 23. The kit has an inexpensive tray 25 which serves as a drain receptacle for the effluvia of the lavage. The drape may have a fastener 24 attached to the periphery 13 for connecting the drape to the drain receptacle 25. The drain receptacle has a bottom 26 and continuous side wall 27 terminating in a lip 28. The kit also has an absorbent pad 29 shaped to fit within the drain receptacle 25. The absorbent pad with conventional super absorbents and/or cellulose fibers increases the amount of liquid the drain receptacle can hold.

The wounded area of the patient's body is placed over the drain receptacle. The drape may then be fastened to the lip of the receptacle to hold the components in place. The drape is fastened to the lavage nozzle for irrigation of the area. After the lavage is completed, all the kit elements may be easily disposed of with the contaminated trash.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A disposable surgical kit for use in irrigation of a wound comprising a surgical drape and a drain receptacle, said drape formed of a transparent sheet of plastic, said sheet having a central portion, a marginal portion and a periphery, said marginal portion surrounding said central portion and extending to said periphery, an aperture in said central portion adapted to form a seal about an irrigation instrument, said drain receptacle having a bottom and integral continuous upstanding sidewall, said sidewall terminating in a lip, an absorbent pad shaped to be placed in said drain receptacle whereby said surgical drape forms an enclosure about a wound and an irrigation instrument with said drain receptacle within said enclosure with said absorbent pad disposed in said drain receptacle, and said periphery of said drape overlapping said lip of said drain receptacle.

2. A disposable surgical kit of claim 1 wherein a flexible fastener is adapted to be connected to said periphery of said drape and said lip of said drain receptacle.

3. A disposable surgical kit of claim 1 wherein a part of said periphery of said drape is connected to said lip.

4. A disposable surgical kit of claim 1 wherein said transparent sheet is coated on one side with a surfactant to shed condensation and water droplets.

5. A disposable surgical kit of claim 1 wherein an opening is formed in said marginal portion of said drape to permit manual access.

6. A disposable surgical kit of claim 5 wherein a flap is connected to said drape about said opening, said flap having at least two opposed edges, one of said edges attached to said drape and the other of said edges being free.

7. A disposable surgical kit of claim 3 wherein an opening is formed in said marginal portion of said drape to permit manual access.

8. A disposable surgical kit of claim 7 wherein a flap is connected to said drape about said opening, said flap having at least two opposed edges, one of said edges attached to said drape, and the other of said edges being free.

* * * * *